US008987171B2

(12) United States Patent
Samarajeewa et al.

(10) Patent No.: US 8,987,171 B2
(45) Date of Patent: Mar. 24, 2015

(54) SELECTIVE HERBICIDES WITH ACTIVATOR ADJUVANTS

(75) Inventors: Deepal Samarajeewa, Victoria (CA); Kim F. Taylor, Victoria (CA)

(73) Assignee: W. Neudorff GmbH KG, Emmerthal (DE)

( * ) Notice: Subject to any disclaimer, the term of this patent is extended or adjusted under 35 U.S.C. 154(b) by 130 days.

(21) Appl. No.: 13/149,336

(22) Filed: May 31, 2011

(65) Prior Publication Data

US 2011/0306495 A1 Dec. 15, 2011

Related U.S. Application Data

(60) Provisional application No. 61/353,837, filed on Jun. 11, 2010.

(51) Int. Cl.

| | |
|---|---|
| ***A01N 57/00*** | (2006.01) |
| ***A01N 37/44*** | (2006.01) |
| ***A01N 25/30*** | (2006.01) |
| ***A01N 59/16*** | (2006.01) |

(52) U.S. Cl.
CPC ................ *A01N 37/44* (2013.01); *A01N 25/30* (2013.01); *A01N 59/16* (2013.01)
USPC .......................................... 504/194; 504/320

(58) Field of Classification Search
CPC ... A01N 2300/00; A01N 25/30; A01N 37/36; A01N 25/22; A01N 57/16; A01N 57/28
USPC ................................................. 504/194, 320
See application file for complete search history.

(56) References Cited

U.S. PATENT DOCUMENTS

| | | | | |
|---|---|---|---|---|
| 5,407,899 | A | 4/1995 | Howell | |
| 6,258,749 | B1 * | 7/2001 | Nonomura | 504/121 |
| 6,258,750 | B1 | 7/2001 | Simpson et al. | |
| 6,271,177 | B1 | 8/2001 | Hudetz | |
| 6,323,153 | B1 | 11/2001 | Smiley | |
| 6,972,273 | B2 | 12/2005 | Sedun et al. | |
| 2004/0062785 | A1 * | 4/2004 | Parker | 424/410 |
| 2012/0309860 | A1 | 12/2012 | Huang | |

FOREIGN PATENT DOCUMENTS

| | | | |
|---|---|---|---|
| CA | 2278383 | A1 | 1/2001 |
| WO | 97/02747 | A1 | 1/1997 |
| WO | 99/25194 | A1 | 5/1999 |
| WO | 01/44236 | A1 | 6/2001 |
| WO | 2001050862 | A1 | 7/2001 |
| WO | 03/073856 | A1 | 9/2003 |
| WO | 2007/030649 | A2 | 3/2007 |

OTHER PUBLICATIONS

International Search Report and Written Opinion mailed Nov. 21, 2011 for Application No. PCT/EP2011/059741 (13 pages).

International Preliminary Report on Patentability mailed Jul. 2, 2012 for Application No. PCT/EP2011/059741 (27 pages).

Jin et al., Application of hydrophilic-lipophilic balance (HLB) number to optimize a compatible non-ionic surfactant for dried aerial conidia of *Beauveria bassiana*?. Biological Control. 2008;46:226-233.

* cited by examiner

*Primary Examiner* — Rebecca Prouty
*Assistant Examiner* — Danielle Sullivan

(57) ABSTRACT

An environmentally compatible, selective herbicidal composition is provided that includes an activator adjuvant for enhancing the efficacy of the composition. While the activator adjuvant can be used in combination with a variety of herbicides, in an exemplary embodiment the herbicidal composition includes a metal chelate that is formed from a transition metal component and at least one chelating agent. The activator adjuvant can enhance, even synergistically effect the efficacy of the composition, while maintaining the selectivity of the herbicide.

13 Claims, No Drawings

SELECTIVE HERBICIDES WITH ACTIVATOR ADJUVANTS

FIELD OF THE INVENTION

The present invention relates to selective herbicide compositions enhanced by activator adjuvants and methods for controlling unwanted vegetation.

BACKGROUND OF THE INVENTION

The selective control of unwanted vegetation, such as, for example, weeds, is a major industry. Vegetation can be controlled using herbicides that are non-selective or selective, and systemic or contact. Non-selective herbicides kill or damage all plants to which they are applied, i.e., both desired and undesired vegetation. In contrast, selective herbicides eliminate or inhibit the growth of unwanted vegetation, while leaving the desired vegetation relatively unharmed. Contact herbicides are applied to the top growth, or portion(s) of the plant located above the soil surface. In contrast, systemic herbicides are initially taken up by the roots and/or the foliage of the plant and subsequently translocated to tissues that are remotely located from the point of application.

At present, there are several common types of selective herbicides on the market. The Phenoxy Acid-Type selective herbicides include 2,4-D (2,4-Dicholorophenoxyacetic acid), 2,4-DP (2,4-Dicholorophenoxypropionic acid, or Dichlorprop), and mecoprop (2-(2-methyl-4-chlorophenoxy) propionic acid). These systemic selective herbicides are initially taken up by the leaves, stem or roots of a plant, and subsequently moved throughout the plant. 2,4-D and 2,4-DP stimulate nucleic acid and protein synthesis and affect enzyme activity, respiration, and cell division, while mecoprop affects enzyme activity and plant growth. The Benzoic Acid-Type selective herbicides include dicamba, another systemic selective herbicide that is initially taken up by the leaves and roots of a plant and subsequently moved throughout the plant. Benzoic Acid-Type selective herbicides are similar to the Phenoxy Acid-Type selective herbicides described above.

Currently, these selective herbicides present major toxicological and environmental concerns. Attempts have been made to create selective herbicides that are effective, yet environmentally safe. Sedun et al. (U.S. Pat. No. 6,972,273) teach of a new class of environmentally safe selective herbicides that includes a transition metal component (Fe, Cu, Zn and/or Mn) and a chelating agent (aminopolycarboxylate, salicylate and/or amino acid). These metal complexones can be applied over an area of established grass and turf in which broadleaf weeds are growing and selectively remove these weeds, leaving the grass unharmed. Smiley (U.S. Pat. No. 6,323,153) teaches using various salts of chelating agents that are capable of forming stable coordination complexes with calcium and magnesium salts to control the growth of various weeds in lawns. Simpson (U.S. Pat. No. 6,258,750) teaches an algaecide, herbicidal and/or fungicidal composition including a metal, the chelating agent, ethylene diamine disuccinic acid (EDDS) or a salt thereof, and a source of calcium and chloride ions. Hudetz (U.S. Pat. No. 6,271,177) teaches a herbicide that combines a sulfonyl urea compound and a water-soluble iron compound, while Sedun (WO 01/50862) discloses a herbicidal composition containing a combination of maleic hydrazide (MH) and carboxylic acids. Each of the above-identified publications describing environmentally safe herbicides is hereby incorporated in its entirety by reference thereto.

While such environmentally safe selective herbicidal compositions have been shown to be effective, such compositions have to be applied at higher concentrations compared to conventional selective herbicides. Thus, there is presently a need for environmentally safe compositions that address one or more of the above-identified problems whilst providing effective control of lawn weeds without harming the lawn grasses.

SUMMARY OF THE INVENTION

The present invention is directed to an environmentally compatible, selective herbicidal composition that comprises a herbicidal component and an amphiphilic activator adjuvant component. In one embodiment, the amphiphilic component can have a Hydrophilic-Lipophilic Balance (HLB) of 10 or greater (for example, at least 11, at least 12, at least 13, at least 14, at least 15, at least 16, at least 17, at least 18, at least 19, or 20). In use, the amphiphilic component synergistically enhances the efficacy of the composition.

The activator adjuvant component may be employed in combination with a variety of herbicides. In this regard, the present inventors have identified that the addition of an activator adjuvant to a herbicidal composition synergistically enhances the efficacy of the composition, while maintaining the selectivity of the herbicide. As a result, the composition may be applied to one or both of undesired and desired vegetation, and will control (e.g. substantially destroy) undesired vegetation while leaving desired vegetation substantially unharmed. In one embodiment, the herbicidal component comprises an environmentally safe herbicide, for example as hereinbefore described. In an exemplary embodiment, the herbicidal composition comprises a metal chelate that is formed from a transition metal component and at least one chelating agent.

In other aspects, a herbicidal composition is provided for selectively controlling undesired vegetation. The herbicidal composition can include as an active ingredient a herbicidally effective amount of a metal chelate formed from at least one transition metal component and at least one chelating agent, and an activator adjuvant at an amount effective to enhance the activity of the active ingredient. The present invention also provides a method that includes contacting a target area with a herbicidal composition of the present invention, and selectively controlling undesired vegetation. In this regard, selectively controlling undesired vegetation means that desired vegetation remains substantially unharmed.

The activator adjuvant may have various forms and typically comprises a lipophilic segment and a hydrophilic segment. In an exemplary embodiment, the activator adjuvant is selected from the group consisting of organosilicates, linear alkylbenzene sulfonates, ethoxylated sorbitan esters, alcohol ethoxylates and combinations thereof. In one embodiment, an organosilicate is employed having a HLB value of at least 12, and/or having a HLB value in the range of 10-15. In another embodiment a linear alkylbenzene sulfonate is employed having a HLB value of at least 15 and/or having a HLB value in the range of 15-20. In yet another embodiment, a ethoxylated sorbitan ester is employed having a HLB value of at least 11 and/or having a HLB value in the range of 10-17. In yet another embodiment, a alcohol ethoxylate is employed having a HLB value of at least 12 and/or having a HLB value in the range of 11-14. In one embodiment, the activator adjuvant comprises an organosilicate, which can be present within the composition at a concentration in a range of about 0.005 to 10% by weight, and more preferably in a range of about 0.01 to 1.5% by weight. In other aspects, the activator adjuvant can be a linear alkylbenzene sulfonate, which can be present within the composition at a concentration in a range of about 0.05 to 10% by weight, and more preferably in a range of about 0.1 to 5% by weight. In yet another embodiment, the activator adjuvant can be an ethoxylated sorbitan ester, which can be present within the composition at a concentration in a range of about 0.01 to 10% by weight, and more preferably in a range of about 0.05% to 5% by weight. In another embodiment, the activator adjuvants can be an alcohol ethoxylate, which can be present within the composition at a concentration in a range of about 0.05% to 10% by weight, and more preferably in a range of 0.1% to 5% by weight.

Various metal chelates may be employed as the herbicidal component, and in an exemplary embodiment the metal chelate is selected from the group consisting of ironhydroxyethylenediaminetriacetic acid, iron ethylenediaminetetraacetic acid, iron gluconic acid, iron glutamicaciddiacetic acid, iron ethylenediaminedisuccinate, iron methylglycinediacetate, iron aminotri(methylenephosphonic acid), iron ethanoldiglycine, iron hydroxyethyldiphosphonic acid, iron iminodisuccinic acid, iron hydroxy iminodisuccinic acid, and combinations thereof. The end use concentration of the metal chelate present within the composition can vary, and in one embodiment the concentration can be the range of about 0.01 and 20% by weight, and more preferably about 0.05 to 10.0% by weight of the composition.

In another embodiment, the chelating agent can be comprise an aminopolycarboxylate selected from the group consisting of diamino cyclohexane tetraacetic acid, ethylenediamine disuccinic acid, ethylenediaminetetraacetic acid, ethanoldiglycine, hydroxyethylenediaminetriacetic acid, methylglycinediacetic acid, glutamicaciddiacetic acid, their salts, and combinations thereof. The chelating agent can be biodegradable. Various transition metals can also be used, including, for example, copper, iron, manganese, nickel, zinc, and combinations thereof. In an exemplary embodiment, the transition metal component contains a metal selected from the group consisting ferric iron, ferrous iron, or combinations thereof.

The herbicidal composition can also include various other components, such as growth regulators, fertilizers, herbicides, thickening agents, humectants, antioxidants, stabilizing agents, wetting agents, sequestrants, solvents, dyes, or combinations thereof. In one embodiment, the composition can include a fertilizer selected from the group consisting of urea ammonium nitrate, ammonium nitrate, urea, ammonium sulfate, and combinations thereof.

In yet another embodiment, a method for selectively controlling undesired vegetation is provided and includes providing a herbicidal composition having a transition metal component, a chelating agent selected from the group consisting of alanine diacetic acid, alkoyl ethylene diamine triacetic acid, aminotri(methylenephosphonic acid), asparticaciddiacetic acid, asparticacidmonoacetic acid, diamino cyclohexane tetraacetic acid, citraconic acid, citric acid, 1,2-diaminopropanetetraacetic acid, 1,3-diamino-2-propanoltetraacetic acid, diethylenetriaminepentaacetic acid, ethanolaminediacetic acid, ethanoldiglycine, ethionine, ethylenediaminediglutaric acid, ethylenediaminedihydroxyphenylacetic acid, ethylenediaminedipropionic acid, ethylenediaminedisuccinic acid, ethylenediaminemonosuccinic acid, ethylenediaminetetraacetic acid, ethyleneglycolaminoethylestertetraacetic acid, glutamicaciddiacetic acid, glyceryliminodiacetic acid, glycinamidedisuccinic acid, glycoletherdiaminetetraacetic acid, 2-hydroxyethyldiacetic acid, hydroxyethylenediaminetriacetic acid, hydroxyiminodiacetic acid, iminodiacetic acid, iminodisuccinic acid, lauroyl ethylene diamine triacetic acid, methylglycinediacetic acid, methyliminodiacetic acid, nitrilotriacetic acid, nitrilotripropionic acid, salicylic acid, serinediacetic acid, their salts, and combinations thereof, and an activator adjuvant selected from the group consisting of organosilicates, linear alkylbenzene sulfonates, ethoxylated sorbitan esters, alcohol ethoxylates, and combinations thereof. The method may include contacting a target area (optionally including desired and/or undesired vegetation) with a herbicidally effective amount of the herbicidal composition such that undesired vegetation is selectively controlled while desired vegetation remains substantially unharmed. In an exemplary embodiment, the transition metal component may contain a metal selected from the group consisting of copper, iron, manganese, nickel, zinc, and combinations thereof.

In other aspects, a method for selectively controlling undesired vegetation is provided and includes providing a herbicidal composition having a metal chelate and an activator adjuvant selected from the group consisting of organosilicates, linear alkylbenzene sulfonates, ethoxylated sorbitan esters, alcohol ethoxylates, and combinations thereof, and contacting a target area (optionally including desired and/or undesired vegetation) with a herbicidally effective amount of the herbicidal composition of the present invention such that undesired vegetation is selectively controlled while desired vegetation remains substantially unharmed.

Unless otherwise noted, all percentages referred to herein are percent by weight.

DETAILED DESCRIPTION OF THE INVENTION

The present invention provides an environmentally compatible, selective herbicidal composition that includes an activator adjuvant that is effective to enhance, and even synergistically enhance, the efficacy of the active ingredient of the herbicidal composition. While the activator adjuvant can be used in combination with a variety of herbicidal compositions, in an exemplary embodiment the herbicidal composition includes an active ingredient in the form of a metal chelate that is formed from a transition metal component and at least one chelating agent. It has been identified by the present inventors that the addition of an activator adjuvant to a selective herbicidal composition will enhance, and even synergistically enhance, the efficacy of the active ingredient, while maintaining the selectivity of the herbicide. As a result, the composition can be applied either to both or one of undesired and desired vegetation and will substantially destroy undesired vegetation while leaving desired vegetation substantially unharmed.

As indicated above, the herbicidal composition of the present invention can have a variety of formulations, and various herbicides known in the art can be modified with the activator adjuvants of the present invention. An example of one such known herbicide is FIESTA™ available from W. Neudorff GmbH, which contains as an active ingredient 4.42% iron, present as iron hydroxyethylenediaminetriacetic acid (FeHEDTA). In one exemplary embodiment, the herbicidal composition contains as a selective herbicidal ingredient a metal chelate that is formed from at least one transition metal component and at least one chelating agent. A chelating agent is an organic molecule that can trap or encapsulate certain highly reactive trace metal cations to prevent the cations from entering into unwanted chemical reactions and forming insoluble compounds. As a result, the chelating agent complexes the metal ions into a soluble but bound form, thus forming a metal chelate that is highly soluble in water and that can be readily taken up by vegetation.

A variety of metal chelates can be used as the active herbicidal ingredient in the composition of the present invention. The metal chelate can contain a variety of metals, but it preferably includes a transition metal ion. Suitable transition metal ions include, for example, copper ions, iron ions, manganese ions, nickel ions, zinc ions, and combinations thereof. In an exemplary embodiment, the metal component is an iron ion. The metal ions can be added in a variety of ionic states. By way of non-limiting example, iron ions used in the present invention can be added as either $Fe^{2+}$ ions, $Fe^{3+}$ ions, and mixtures thereof. Various chelating agents can be used to form the metal chelate. A chelating agent is a substance whose molecules can usually form more than one bond to a single metal ion. In other words, a chelating agent is usually a multidentate ligand. By way of non-limiting example, suitable chelating agents include aconitic acid, alanine diacetic acid (ADA), alkoyl ethylene diamine triacetic acids (e.g., lauroyl ethylene diamine triacetic acids (LED3A), aminotri (methylenephosphonic acid) (ATMP), asparticaciddiacetic acid (ASDA), asparticacidmonoacetic acid, diamino cyclohexane tetraacetic acid (CDTA), citraconic acid, citric acid, 1,2-diaminopropanetetraacetic acid (DPTA-OH), 1,3-diamino-2-propanoltetraacetic acid (DTPA), diethanolamine, diethanol glycine (DEG), diethylenetriaminepentaacetic acid (DTPA), diethylene triamine pentamethylene phosphonic acid (DTPMP), diglycolic acid, dipicolinic acid (DPA), ethanolaminediacetic acid, ethanoldiglycine (EDG), ethionine, ethylenediamine (EDA), ethylenediaminediglutaric acid (EDDG), ethylenediaminedi(hydroxyphenylacetic acid (EDDHA), ethylenediaminedipropionic acid (EDDP), ethylenediaminedisuccinate (EDDS), ethylenediaminemonosuccinic acid (EDMS), ethylenediaminetetraacetic acid (EDTA), ethylenediaminetetrapropionic acid (EDTP), ethyleneglycolaminoethylestertetraacetic acid (EGTA), gallic acid, glucoheptonic acid, gluconic acid, glutamicaciddiacetic acid (GLDA), glutaric acid, glyceryliminodiacetic acid, glycinamidedisuccinic acid (GADS), glycoletherdiaminetetraacetic acid (GEDTA), 2-hydroxyethyldiacetic acid, hydroxyethylenediaminetriacetic acid (HEDTA), hydroxyethyldiphosphonic acid (HEDP), 2-hydroxyethyl imino diacetic acid (HIMDA), hydroxyiminodiacetic acid (HIDA), hydroxyiminodisuccinic acid (HIDS), 2-hydroxy propylene diamine disuccinic acid (HPDDS), iminodiacetic acid (IDA), iminodisuccinic acid (IDS), itaconic acid, lauroyl ethylene diamine triacetic acids (LED3A), malic acid, malonic acid, methylglycinediacetate (MGDA), methyliminodiacetic acid (MIDA), monoethanolamine, nitrilotriacetic acid (NTA), nitrilotripropionic acid (NPA), N-phosphonomethyl glycine (glyphosate), propyldiamine tetraacetic acid (PDTA), salicylic acid, serinediacetic acid (SDA), sorbic acid, succinic acid, sugars, tartaric acid, tartronic acid, triethanolamine, triethylenetetraamine, triethylene tetraamine hexaacetic acid (TTHA), and combinations thereof. In an exemplary embodiment, the chelating agent is EDTA, HEDTA, EDG, EDDS, GLDA MGDA, isomers thereof, and combinations thereof. Other suitable chelating agents include aminopolycarboxylic acid, amines, amides, phosphonic acid, and combinations thereof. Amino acids can also be used as chelating agents. Suitable amino acids include alanine, arginine, asparagine, aspartic acid, glutamic acid, glutamine, glycine, histidine, isoleucine, leucine, lysine, methionine, proline, serine, threonine, tyrosine, valine, and combinations thereof. Other suitable chelating agents that can be used in the herbicidal compositions of the present invention include beet molasses, carboxylic acids and the salts thereof, salicylic acid and the salts thereof (such as ammonium salicylate), citric acid, humic acid, and combinations thereof.

The metal chelate can be formed using various techniques known in the art. For example, the metal ions can be in the form of a metal salt, such as metal chlorides, metal sulfates, metal nitrates, metal citrates, metal phosphates, metal chelates, metal sulfides, metal sulfites, metal succinates, metal gluconates, metal lactates, metal formates, metal nitrites, metal salicylates, metal carboxylic acids, and in combinations of these salts. The chelating agent can also have various forms. In one embodiment, the chelating agent can be a free acid. In another embodiment the chelating agent can be a salt. Preferably, in this embodiment, the chelating agent is added as a sodium salt, potassium salt, calcium salt, ammonium salt, amine salt, amide salt, and combinations thereof. In another embodiment, the chelating agent can be added as an alkali metal chelate, including calcium and magnesium. Commercially available metal chelates can also be used.

In certain embodiments, chelating agents that are more readily biodegradable are used in the compositions of the present invention. Such chelating agents include ATMP, EDG, EDDS, GLDA, HEDP, MGDA, IDS, and HIDS. Chelating agents found in nature in plants can also be more likely to biodegrade as well, including, for example, citric acid, gallic acid, glutaric acid, malic acid, salicylic acid, sorbic acid, succinic acid, sugars, and tartaric acid. Some amino acids can also more easily biodegradable, such as alanine, arginine, asparagine, aspartic acid, glutamic acid, glutamine, glycine, histidine, isoleucine, leucine, lysine, methionine, proline, serine, threonine, tyrosine, and valine.

As indicated above, the herbicidal composition can also include an amphiphilic activator adjuvant. In an exemplary embodiment, the activator adjuvant has a Hydrophilic-Lipophilic Balance (HLB) of 10 or greater which is capable of synergistically enhancing the efficacy of a selective herbicidal ingredient applied to unwanted plants. The balance or relative effect of these segments on the overall physical and chemical properties of the activator adjuvant is herein described by reference to a HLB value. HLB is a recognized term of art for non-ionic surfactants (see Griffin W C: "Calculation of HLB Values of Non-Ionic Surfactants," Journal of the Society of Cosmetic Chemists 5 (1954): 259), and is typically defined as follows:

$$HLB=20*Mh/M$$

where Mh is the molecular mass of the hydrophilic portion of the Molecule, and M is the molecular mass of the whole molecule, giving a result on an arbitrary scale of 0 to 20. An HLB value of 0 corresponds to a completely hydrophobic molecule, and a value of 20 corresponds to a molecule made up completely of hydrophilic components. Without wishing to be bound by any theory, the present inventors believe that the adjuvants of the present invention having high HLB values (e.g. 10 or higher) are advantageously absorbed into the cuticle and enhance water holding capacity (hydration state) of the cuticle. In this regard, herbicide absorption into and through the cuticle is primarily limited to the amount of herbicide in solution on the leaf surface. Thus, an increased cuticle hydration is believed to lead to increased permeation of the herbicide component of the present invention (e.g. a hydrophilic herbicide) into the cuticle, which, in turn, increases the herbicide diffusion rate at a concentration gradient (Hess and Foy Weed Tech 2000. Vol. 14:807-813).

In one embodiment, the amphiphilic adjuvant component has a HLB value in the range of 10-20, for example, 12-20, 14-20, 16-20, 12-18, 12-16, or 14-18. The present inventors have identified, and it is particularly surprising, that the addition of an adjuvant component to a herbicidal composition in accordance with the present invention provides an enhanced, and even synergistic effect, on undesirable vegetation whilst a corresponding enhanced (e.g. synergistic) effect is not observed on desired vegetation. In other words, the effect of herbicide and the adjuvant combined is greater than the sum of the individual effect of the herbicidal active ingredient and the activator adjuvant. This is further demonstrated in the examples set forth below, and as shown the activator adjuvant substantially increases the efficacy of the selective herbicidal active ingredient on undesired vegetation, while leaving desired vegetation substantially unharmed.

While the activator adjuvant can have various forms, in an exemplary embodiment it is an amphiphilic activator adjuvant with a HLB of 10 or greater, for example 10-17 or 11-16, such that it possesses both hydrophilic and lipophilic properties. For example, the activator adjuvant can be an organic, amphiphilic additive, such as an amphiphilic surfactant. It is believed that combined hydrophilic and lipophilic nature of the activator adjuvant facilitates transport of the herbicide through the plant's cuticle. Unique blend of lipophilic and hydrophilic properties of the surfactants can serve as a solvent for herbicides on the leaf surface and the surfactants that maintain herbicides in a soluble form on the leaf surface increase the driving force (concentration gradient) across the cuticle.

The activator adjuvant can be added to the herbicidal composition at the time of formulation, or it can be provided as a separate composition that is mixed with the herbicide prior to or during application or that is applied separately to the vegetation.

In one embodiment, the activator adjuvant can be a polyoxyalkylene polysiloxane surfactant (e.g. 3-(3-Hydroxypropyl)heptamethyltrisiloxane, ethoxylated acetate, polyethylene glycol monallyl acetate and/or polyethylene glycol diacetate, and combinations thereof such as a composition comprising all of said five components). Examples of suitable commercial organosilicone non-ionic surfactants include Sylgard® 309 available from Dow Corning Corp., Midland, Mich. 48686, Break Thru® available from Evonik Degussa Corp., Parsippany, N.J. 07054, Q2-5211® Super wetting agent available from Dow Corning Corp., Midland, Mich. 48686.

In another embodiment, the activator adjuvant can be a linear alkylbenzene sulfonate (LAS) such as Bio-Soft® D-40 (sodium dodecylbenzene sulfonate) available from Stephan Co., Northfield, Ill. 60093, or Calsoft® F-90 available from Pilot Chemical Co., Cincinnati, Ohio 45241, and combinations thereof. It is a readily biodegradable surfactant widely used in household, industrial, and institutional detergent industries.

In yet another embodiment, the activator adjuvant can be an ethoxylated sorbitan ester (e.g. polyoxyethylene sorbitans) such as Tween® 20 [polyoxyethylene (20) sorbitan monolaurate], Tween® 21 [polyoxyethylene (4)sorbitan monolaurate], Tween®40 [polyoxyethylene (20) sorbitan monopalmitate], Tween® 80 [polyoxyethylene (20)-sorbitan monooleate], Tween® 81 [polyoxyethylene (5) sorbitan monooleate], and Tween® 85 [polyoxyethylene (20) sorbitan trioleate], and combinations thereof, all available from Croda Canada Ltd., Racco Parkway Vaughan, Ontario L4J 8X9. Many liquid polysorbate surfactants display mammalian and ecological safety, biodegradability, excellent physical properties, ease of formulation, superior dilution performance, and virtually no phytotoxicity.

In yet another embodiment, the activator adjuvant can be an alcohol ethoxylate (e.g. alcohol C5-15 ethoxylates) such as Bio-Soft N 25-7 [alcohols (C12-15 Ln saturated) ethoxylate], Bio-Soft N 1-7 [alcohols (C11 Ln saturated) ethoxylate], Bio-Soft N 23-6.5 [alcohols, C12-13, ethoxylated], Bio-Soft N 91-8 (alcohols, (C9-11 Ln saturated) ethoxylate), Makon TD-12 (tridecyl alcohol ethoxylate), Polystep TD-189 (tridecyl alcohol ethoxylate), and combinations thereof, all available from Stephan Co., Northfield, Ill. 60093. Alcohol ethoxylates (AE) are nonionic surfactants composed of an alkyl chain (usually 12 to 15 carbons) combined with some ethylene oxide units (3-14). AEs are readily biodegradable under aerobic and anaerobic conditions.

In another aspect, a eucalyptus oil and/or an esterified seed oil can be used as the activator adjuvant. A eucalyptus oil is a complex mixture of a variety of monoterpenes and sesquiterpenes, and aromatic phenols, oxides, ethers, alcohols, esters, aldehydes, and ketones. The esterified seed oil, can be, for example Methylated Seed Oil (MSO®) Concentrate with LECI-TECH™ available from Loveland Products Inc., Greeley, Colo. 80632-1286.

The end-use concentration of the ingredients of the herbicidal compositions of the present invention can vary depending on the form of the metal chelate and the activator adjuvant. When referring to the amount, e.g., concentration and molar ratio, of the metal component in the composition, the amount is based on the amount of metal ions present within the metal component.

Where the active ingredient in the selective herbicidal composition is a metal chelate, the end use concentration of the metal chelate in the composition can vary significantly. By way of non-limiting example, the concentration of metal chelate applied to the plant can be in the range of about 0.01 and 20% by weight, and more preferably about 0.05 to 10.0% by weight of the composition. The concentration of the metal ion present in the metal chelate can also vary. For example, the molar ratio of metal to chelating agent can be substantially equal to one, greater than one, substantially greater than one, less than one, or substantially less than one. More preferably, the molar ratio of metal to chelating agent is in the range of about 0.05:1 to 20:1, and more preferably is about 0.2:1 to 5:1. In an exemplary embodiment, the concentration of metal ions present in the herbicidal composition applied to the plant is preferably in the range of about 0.01 to 5.0% by weight, and more preferably about 0.05 to 2.0% by weight.

The concentration of the activator adjuvant in the herbicidal composition can also vary. In accordance with one embodiment, the formulation can include a polyoxyalkylene polysiloxane activator adjuvant present at a concentration in a range of about 0.005 to 10% by weight, and more preferably about 0.01 to 1.5% by weight. In another embodiment, the composition can include a linear alkylbenzene sulfonate activator adjuvant present at a concentration in a range of about 0.05 to 10% by weight, and more preferably about 0.1 to 5% by weight. In yet another embodiment, the composition can include an ethoxylated sorbitan ester activator adjuvant present at a concentration in a range of about 0.01 to 10%, and more preferably about 0.05% to 5% by weight. In another embodiment, the activator adjuvants can be an alcohol ethoxylate, which can be present within the composition at a concentration in a range of about 0.05% to 10% by weight, and more preferably in a range of 0.1%-5% by weight.

Besides the above ingredients, a variety of other components can optionally be added to the selective herbicide compositions. By way of non-limiting example, these additives can include fertilizers, growth regulators, amino acids, additional herbicides, thickening agents, dyes, and combinations thereof.

A variety of fertilizers can be added to the herbicidal composition of the present invention. Preferably, the fertilizer is a nitrogen-containing fertilizer that is effective to promote the rapid growth of grass, thereby allowing the grass to shade and out-compete the damaged weeds. The fertilizer can be added as a commonly used fertilizer such as urea ammonium nitrate, ammonium nitrate, urea, ammonium sulfate. The end-use concentration of added fertilizer(s) can vary, but preferably, the concentration of fertilizer is in the range of about 0.1 to 5% by weight.

A variety of growth regulators may also be added to the herbicidal composition of the present invention. By way of non-limiting example, the growth regulators added to the herbicidal compositions can include maleic hydrazide (MH), cyclocel (2-chloroethyl-trimethyl ammonium chloride), auxin derivatives, and combinations thereof. The end-use concentration of the additional growth regulators can vary, but preferably, the concentration is between about 100 ppm and 2% by weight.

The herbicidal compositions of the present invention can also include natural growth regulators, such as for example, salicylic acid, salts of salicylic acid including ammonium salicylate, jasmonates, ethylene, auxins, gibberellins, cytokinins, abscisic acid, and combinations thereof. The end-use concentration of these natural growth regulators can vary, but preferably, the concentration is between about 10 ppm and 5% by weight.

In addition to the selective herbicides disclosed herein, the herbicidal compositions of the present invention can include other herbicides as a co-active ingredient. The co-active ingredients that can be added as additional herbicides include glyphosate, glufosinate, fatty acids and salts thereof, urea, sodium, borax, copper sulfate, carboxylic acids and the salts thereof, ammonium salts, calcium salts, and combinations thereof. The end-use concentration of the additional herbicide (s) can vary, but preferably, the concentration is in the range of about 100 ppm to 5% by weight.

Furthermore, a variety of thickening agents may be added to the herbicidal compositions disclosed herein. Preferably, these thickening agents include Rhodopol 23 (Rhone Poulenc), VanGel B (R. T. Vanderbilt), Kelzan S (Merck & Co.), guar gum, propylene glycol, glycerol, and combinations thereof. The end-use concentration of added thickening agent (s) can vary, but preferably, the concentration is in the range of about 0.01 to 10% by weight.

Other additives may be included in the herbicidal compositions disclosed herein. By way of non-limiting example, a herbicidal composition according to the present invention can include humectants, antioxidants, stabilizing agents, wetting agents, sequestrants, preservatives and combinations thereof. Suitable humectants include, for example, propylene glycol, glycerin, beet molasses, and combinations thereof. Suitable antioxidants include, for example, citric acid, while suitable stabilizing agents include citric acid, ammonium salts, and combinations thereof. Suitable wetting agents include, for example, carboxylic acids and the salts thereof and silicone polymers such as Silwet 77 (Witco Corp, CT, USA). Suitable preservatives include Kathon® (a mixture of 5-chloro-2-methyl-4-isothiazolin-3-one and 2-methyl-4-isothiazolin-3-one, made by Rohm & Haas of Hayward, Calif.), sorbic acid, sodium benzoate, sodium propionate, parabens, isopropyl alcohol and ethanol. The end-use concentration of these additives may vary, but preferably, the concentration is between about 0.1 and 5% by weight.

In use, the formulation of the selective herbicide of the present invention can vary. Preferably, the herbicidal compositions are provided (optionally as a ready-to-use formulation) as a liquid composition, a dry granule, a liquid concentrate, or a dry concentrate. The solvents used in the ready-to-use liquid composition and liquid concentrate forms can vary. Preferably, the solvent is a poor wetting agent on plant leaves, essentially equal to that of water. Grass leaves are often vertical and hard to wet, whereas many weeds, such as the dandelion, are horizontal and easier to wet. Solutions that are poor wetting agents are advantageous because they tend to bead up and run off of grass leaves, while spreading onto leaves of the horizontal weeds, such as the dandelion. More preferably, the solvent(s) used in the formulation of the disclosed herbicidal compositions are propylene glycol, glycerin, alcohols such as tetrahydrofurfuryl alcohol (THFA) and combinations thereof.

The pH of the herbicidal solution can vary, but preferably, the herbicidal compositions of the present invention are effective over a wide range of pH values. More preferably, the pH of the herbicidal compositions of the present invention is between about 1.5 and 10. After the formulation has been prepared, the pH of the solution can be measured and adjusted as necessary. The pH values can be measured using standard pH meters, with glass bulb electrodes.

A typical formulation, for example a ready-to-use (RTU) formulation, according to one embodiment of the present invention is as follows:

| |
|---|
| 1.5% FeHEDTA |
| 0.1% Sylgard ® 309 |
| 0.08% sodium citrate stabilizer |
| 0.07% Kathon CG preservative |
| 98.25% deionized water |

The formulation is prepared by adding water to a vessel, and adding FeHEDTA concentrate to the water by stirring. Once thoroughly mixed, the activator adjuvant (e.g., Sylgard® 309), stabilizer sodium citrate, and preservative Kathon CG are added to the solution and the composition is stirred until the solution is homogeneous. Further additives, if used, such as fertilizers can be added at this stage and mixing continued. The solution can be sprayed onto both desired and undesired vegetation using a hand sprayer at various rates. In an exemplary embodiment, the solution is sprayed at a rate in the range of about 25 $ml/m^2$ to 800 $ml/m^2$, and more preferably in the range of about 40 $ml/m^2$ to 400 $ml/m^2$, and most preferably at a rate of about 200 $ml/m^2$.

Desired vegetation can include grass, lawn, and/or pastureland. Thus, in use, the composition of the present invention does not cause any substantial damage to one or more of (e.g. all of) grass, lawn and/or pastureland. Undesired vegetation can include weeds and unwanted plants in lawns, including dicotyledonous plants, monocotyledonous plants, conifers, cycads, ferns, horsetails, mosses, liverworts, and algae. Thus, in use, the composition of the present invention controls one or more of (e.g. all of) weeds and unwanted plants in lawns, including dicotyledonous plants, monocotyledonous plants, conifers, cycads, ferns, horsetails, mosses, liverworts, and algae. The composition can be used in both residential and commercial plant or crop areas, and it is very effective against one or more of (e.g., all of) common weeds such as dandelions (*Taraxacum officinale*), false dandelions (*Hypochoeris radicata*), white clover (*Trifolium repens*), daisies (*Bellis perennis*), and chickweed (*Stellaria media*).

The following non-limiting examples serve to further describe the invention. Unless otherwise specified, all of the iron solutions were made using the same molar concentration of iron ion as chelating agent. Samples were prepared by diluting a metal chelate, such as iron GLDA (Dissolvine GL-Fe-5), iron EDDS (Enviomet C320), or iron HEDTA (Neu 1173H), to the desired level of iron as specified using simple stirring. Neu 1173H contains the stabilizer sodium citrate at 1.5% prior to dilution. Dilutions of Neu1173H to the level of 0.25% Fe, incorporates 0.08% sodium citrate into the spray solutions. Adjuvants (Sylgard® 309, Biosoft®D-40, Tween® 20), were then diluted and added to the diluted metal chelate. Samples were usually prepared within 48 hours of spraying. All of the outside tests were done on areas of mixed grass and white clover that were at least 2 months old. For the greenhouse tests, white clover and black medic were grown in a commercial greenhouse mix using supplemental lighting and heating. Each plant was grown in a 2¼ inch pot to a minimum diameter of 15-20 cm. Perennial ryegrass was grown in 2¼ inch pots in the same greenhouse conditions as above and they are at least 4 weeks old at the time of application. Field and greenhouse trials had at least two and ten replicates respectively. All of the solutions were sprayed onto the plants at a rate of 200 ml/m$^2$ using a handheld trigger sprayer.

All plant damage was visually assessed using a percentage rating scale from 0 (no injury) to 100% (death). A damage rating of 40% or higher may be high enough to control undesired plants.

EXAMPLE 1

Greenhouse White Clover and Turf Test of Iron Chelates with Polyoxyalkylene Polysiloxane (Sylgard® 309) Activator Adjuvant All of the iron chelates (0.4% Fe) and the activator adjuvant were sprayed twice at a volume of 200 ml/m$^2$ on to 0.25 m$^2$ areas of perennial ryegrass and white clover. Observations were made 7 days after second spraying. The results are shown in Table 1 below.

TABLE 1

| | Grass Damage (%) | White Clover Damage (%) |
|---|---|---|
| Sylgard ® 309 (0.1%) | 4 | 0 |
| FeEDDS 2.49% a.i. (0.4% Fe) | 3 | 27 |
| FeGLDA 2.28% a.i. (0.4% Fe) | 8 | 7 |
| FeEDDS 2.49% a.i. (0.4% Fe) + Sylgard ® 309 (0.1%) | 4 | 42 |
| FeGLDA 2.28% a.i. (0.4% Fe) + Sylgard ® 309 (0.1%) | 9 | 44 |
| Untreated | 0 | 0 |

EXAMPLE 2

Greenhouse Black Medic and Turf Test of Iron Chelates with Polyoxyalkylene Polysiloxane (Sylgard® 309) Activator Adjuvant All of the iron chelates (0.25% and 0.4% Fe) and the activator adjuvant were sprayed twice at a volume of 200 ml/m$^2$ on to 0.25 m$^2$ areas of perennial ryegrass and black medic. Observations were made 7 days after first spraying. The results are shown in Table 2 below.

TABLE 2

| | Grass Damage (%) | Black Medic Damage (%) |
|---|---|---|
| FeEDDS 2.49% a.i. (0.4% Fe) | 2 | 28 |
| FeEDDS 2.49% a.i. (0.4% Fe) + Sylgard ® 309 (0.1%) | 6 | 82 |
| FeHEDTA 1.5% a.i (0.25% Fe) | 3 | 54 |
| FeHEDTA 1.5% a.i (0.25% Fe) + | 8 | 86 |

TABLE 2-continued

| | Grass Damage (%) | Black Medic Damage (%) |
|---|---|---|
| Sylgard ® 309 (0.1%) | | |
| Untreated | 0 | 0 |

EXAMPLE 3

Greenhouse White Clover and Turf Test of Iron Chelates with Linear Alkylbenzene Sulfonate (Bio-Soft® D-40) Activator Adjuvant All of the iron chelates (0.4% Fe) and the activator adjuvant were sprayed twice at a volume of 200 ml/m$^2$ on to 0.25 m$^2$ areas of perennial ryegrass and white clover. Observations were made one day after first spraying. The results are shown in Table 3 below.

TABLE 3

| | Grass Damage (%) | White Clover Damage (%) |
|---|---|---|
| Bio-Soft ® D-40 (1%) | 0 | 0 |
| FeGLDA 2.28% a.i. (0.4% Fe) | 0 | 8 |
| FeEDDS 2.49% a.i. (0.4% Fe ) | 1 | 15 |
| FeGLDA 2.28% a.i. (0.4% Fe) + Bio-Soft ® D-40 (1%) | 2 | 40 |
| FeEDDS 2.49% a.i. (0.4% Fe) + Bio-Soft ® D-40 (1%) | 5 | 50 |
| Untreated | 0 | 0 |

EXAMPLE 4

Field White Clover and Turf Test of Iron Chelates with Linear Alkylbenzene Sulfonate (Bio-Soft® D-40) Activator Adjuvant All of the iron chelates (0.4% Fe) and the activator adjuvant were sprayed twice at a volume of 200 ml/m$^2$ on to 0.25 m$^2$ areas of park lawn and white clover. Observations were made 14 days after second spraying. The results are shown in Table 4 below.

TABLE 4

| | Grass Damage (%) | White Clover Damage (%) |
|---|---|---|
| FeEDDS 2.49% a.i. (0.4% Fe) | 1 | 38 |
| FeEDDS 2.49% a.i. (0.4% Fe) + Bio-Soft ® D-40 (0.1%) | 5 | 78 |
| Untreated | 0 | 0 |

EXAMPLE 5

Greenhouse White Clover and Turf Test of Iron Chelates with Ethoxylated Sorbitan Ester (Tween® 20) Activator Adjuvant All of the iron chelates (0.4% Fe) and the activator adjuvant were sprayed twice at a volume of 200 ml/m$^2$ on to 0.25 m$^2$ areas of perennial ryegrass and white clover. Observations were made one day after first spraying. The results are shown in Table 5 below.

TABLE 5

| | Grass Damage (%) | White Clover Damage (%) |
|---|---|---|
| Tween ® 20 (0.23%) | 0 | 5 |
| FeEDDS 2.49% a.i. (0.4% Fe) | 0 | 18 |
| FeEDDS 2.49% a.i. (0.4% Fe) + Tween ® 20 (0.23%) | 1 | 55 |
| Untreated | 0 | 0 |

EXAMPLE 6

Greenhouse White Clover and Turf Test of Iron Chelates with Polyoxyalkylene Polysiloxane (Sylgard® 309) Activator Adjuvant All of the iron chelates (0.25% Fe) and the activator adjuvant were sprayed twice at a volume of 200 ml/$m^2$ on to 0.25 $m^2$ areas of perennial ryegrass and white clover. Observations were made 14 days after second spraying. The results are shown in Table 6 below.

TABLE 6

| | Grass Damage (%) | White Clover Damage (%) |
|---|---|---|
| FeHEDTA 1.5% a.i (0.25% Fe) | 2 | 46 |
| FeHEDTA 1.5% a.i (0.25% Fe) + Sylgard ® 309 (0.1%) | 3 | 88 |
| Untreated | 0 | 0 |

EXAMPLE 7

Greenhouse Dandelion and Turf Test of Iron Chelates with Polyoxyalkylene Polysiloxane (Sylgard® 309) Activator Adjuvant All of the iron chelates (0.4% Fe) and the activator adjuvant were sprayed twice at a volume of 200 ml/$m^2$ on to 0.25 $m^2$ areas of perennial ryegrass and dandelion. Observations were made 7 days after first spraying. The results are shown in Table 7 below.

TABLE 7

| | Grass Damage (%) | Dandelion Damage (%) |
|---|---|---|
| FeGLDA 2.28% a.i. (0.4% Fe) | 6 | 38 |
| FeGLDA 2.28% a.i. (0.4% Fe) + Sylgard 309 ® (0.1%) | 5 | 64 |
| Untreated | 0 | 0 |

EXAMPLE 8

Field English Daisy and Turf Test of Iron Chelates with Polyoxyalkylene Polysiloxane (Sylgard® 309) Activator Adjuvant All of the iron chelates (0.4% Fe) and the activator adjuvant were sprayed twice at a volume of 200 ml/$m^2$ on to 0.25 $m^2$ areas of park lawn and English daisy. Observations were made 5 days after first spraying. The results are shown in Table 8 below.

TABLE 8

| | Grass Damage (%) | English daisy Damage (%) |
|---|---|---|
| FeEDDS 2.49% a.i. (0.4% Fe) | 4 | 39 |
| FeEDDS 2.49% a.i. (0.4% Fe) + Sylgard ® 309 (0.1%) | 7 | 73 |
| Untreated | 0 | 0 |

EXAMPLE 9

Field English Daisy and Turf Test of Iron Chelates with Polyoxyalkylene Polysiloxane (Sylgard® 309), and Linear Alkylbenzene Sulfonate (Bio-Soft® D-40)

All of the iron chelates (0.25% Fe) and the activator adjuvants were sprayed twice at a volume of 100 ml/$m^2$ on to 0.25 $m^2$ areas of park lawn and English daisy. Observations were made 7 days after first spraying. The results are shown in Table 9 below.

TABLE 9

| | Application rate (ml/$m^2$) | Grass Damage (%) | English daisy Damage (%) |
|---|---|---|---|
| FeHEDTA 1.5% a.i (0.25% Fe) | 100 | 2 | 81 |
| FeHEDTA 1.5% a.i (0.25% Fe) + Sylgard ® 309 (0.1%) | 100 | 3 | 90 |
| FeHEDTA 1.5% a.i (0.25% Fe) + Bio-Soft ® D-40 (1%) | 100 | 6 | 95 |
| Untreated | | 0 | 0 |

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

Reference to "control" embraces growth suppression, growth prevention, cellular damage and/or death of vegetation. Reference to "control" embraces prophylactic and treatment regimens.

Reference to "target area" simply means the area to which the formulations of the present invention are applied, and embraces adjacent areas into which the formulations may disperse. Examples of dispersion include application into a liquid-containing environment, and dispersion onto a solid surface with associated dilution (e.g. by weathering).

What is claimed is:

1. A herbicidal composition comprising:

(a) an active ingredient comprising a metal chelate formed from at least one transition metal component comprising iron, and at least one chelating agent comprising an aminopolycarboxylic acid; and (b) an amphiphilic activator adjuvant to enhance the activity of the active ingredient, the amphiphilic activator adjuvant comprising an organosilicate having a Hydrophilic-Lipophilic Balance value of at least 11.

2. The herbicidal composition of claim 1, wherein the herbicidal composition selectively controls undesired vegetation.

3. The herbicidal composition of claim 1, wherein the chelating agent comprises an aminopolycarboxylic acid selected from the group consisting of diamino cyclohexane tetraacetic acid, ethylenediamine disuccinic acid, ethylenediaminetetraacetic acid, ethanoldiglycine, hydroxyethylenediaminetriacetic acid, methylglycinediacetic acid, glutamicaciddiacetic acid, their salts, and combinations thereof.

4. The herbicidal composition of claim 1, wherein the amphiphilic activator further comprises a second amphiphilic activator selected from the group consisting of: a polyoxyalkylene polysiloxane surfactant, a linear alkylbenzene sulfonate, a polyoxyethylene sorbitan, an alcohol C5-15 ethyoxylate, and combinations thereof.

5. The herbicidal composition of claim 1, wherein the composition comprises Fe-hydroxyethylenediaminetriacetic acid and/or Fe-ethylenediaminedisuccinic acid and/or Fe-glutamicaciddiacetic acid as the active ingredient and further comprising a polyoxyalkylene polysiloxane surfactant as a second activator adjuvant.

6. The herbicidal composition of claim 1, wherein the composition comprises Fe-hydroxyethylenediaminetriacetic acid and/or Fe-ethylenediaminedisuccinic acid and/or Fe-glutamicaciddiacetic acid as the active ingredient and further comprising an alcohol ethoxylate as a second activator adjuvant.

7. The herbicidal composition of claim 1, wherein the composition comprises Fe-hydroxyethylenediaminetriacetic acid and/or Fe-ethylenediaminedisuccinic acid and/or Fe-glutamicaciddiacetic acid as the active ingredient and further comprising polyoxyethylene sorbitan as a second activator adjuvant.

8. The herbicidal composition of claim 1, wherein the composition comprises Fe-hydroxyethylenediaminetriacetic acid and/or Fe-ethylenediaminedisuccinic acid and/or Fe-glutamicaciddiacetic acid as the active ingredient and further comprising an alkyl benzenesulfonate as a second activator adjuvant.

9. The herbicidal composition of claim 1, wherein the herbicidal composition does not substantially harm desired vegetation.

10. The herbicidal composition of claim 1, wherein the chelating agent comprises an ethylenediaminedisuccinic acid.

11. The herbicidal composition of claim 1, wherein the chelating agent comprises a glutamicaciddiacetic acid.

12. The herbicidal composition of claim 1, wherein the chelating agent comprises an ethylenediaminedisuccinic acid and a glutamicaciddiacetic acid.

13. A method of controlling vegetation, the method comprising contacting a target area with the herbicidal composition of claim 1.

* * * * *